(12) United States Patent
Cawley et al.

(10) Patent No.: US 8,391,958 B2
(45) Date of Patent: Mar. 5, 2013

(54) METHOD AND ARRANGEMENT RELATING TO TESTING OBJECTS

(75) Inventors: Peter Cawley, London (GB); Anders Pettersson, Gothenburg (SE)

(73) Assignee: Osstell AB, Gothenburg (SE)

( * ) Notice: Subject to any disclaimer, the term of this patent is extended or adjusted under 35 U.S.C. 154(b) by 43 days.

(21) Appl. No.: 12/393,931

(22) Filed: Feb. 26, 2009

(65) Prior Publication Data
US 2009/0299173 A1   Dec. 3, 2009

Related U.S. Application Data

(63) Continuation-in-part of application No. 10/561,362, filed as application No. PCT/SE2004/000998 on Jun. 21, 2004, now abandoned.

(30) Foreign Application Priority Data

Jun. 19, 2003  (SE) ...................................... 0301825

(51) Int. Cl.
    *A61B 6/00*  (2006.01)
(52) U.S. Cl. ........ 600/431; 600/407; 600/424; 600/437; 600/587; 600/590
(58) Field of Classification Search .................. 600/302, 600/587, 594, 595, 407, 424, 431, 590; 623/16, 623/18.11, 18.12; 433/167, 173
    See application file for complete search history.

(56) References Cited

U.S. PATENT DOCUMENTS

| | | | |
|---|---|---|---|
| 3,292,426 A * | 12/1966 | McCann | 73/658 |
| 3,355,933 A | 12/1967 | Rowe | |
| 3,474,314 A * | 10/1969 | Ito | 318/128 |
| 3,580,056 A * | 5/1971 | Warner | 73/579 |
| 3,603,137 A * | 9/1971 | Banks | 73/32 R |
| 4,362,511 A | 12/1982 | Jacklich | |
| 4,511,330 A * | 4/1985 | Smiley et al. | 433/18 |
| 4,644,310 A | 2/1987 | Anderson, III et al. | |
| 4,682,608 A * | 7/1987 | De Rigal et al. | 600/587 |
| 4,815,975 A * | 3/1989 | Garrel et al. | 433/189 |
| 4,922,444 A | 5/1990 | Baba | |
| 5,055,786 A | 10/1991 | Wakatsuki et al. | |
| 5,392,779 A * | 2/1995 | Meredith et al. | 600/437 |
| 5,518,008 A * | 5/1996 | Cucchiaro et al. | 600/590 |
| 5,552,778 A | 9/1996 | Schrott et al. | |
| 5,680,874 A * | 10/1997 | Takuno | 600/587 |
| 6,032,677 A * | 3/2000 | Blechman et al. | 128/899 |
| 6,034,296 A * | 3/2000 | Elvin et al. | 623/16.11 |
| 6,161,046 A * | 12/2000 | Maniglia et al. | 607/57 |

(Continued)

FOREIGN PATENT DOCUMENTS

| | | |
|---|---|---|
| EP | 0602970 A2 | 6/1994 |
| EP | 0702942 A1 | 3/1996 |

(Continued)

*Primary Examiner* — Rene Towa
(74) *Attorney, Agent, or Firm* — Pierce Atwood LLP

(57) ABSTRACT

The invention relates to an arrangement (100, 200, 500) and a method for testing a hold (120, 220, 520), such as an implant, attached to an object (130, 230, 530), such as a bone, the method comprising the steps of: bringing a member (110, 210, 510) into contact with said hold, contactlessly detecting at least one resonance frequency of said member (110, 210, 510) when it is in contact with said hold (120, 220, 510); and interpreting the detected resonance frequency in terms of the degree of attachment of the hold with respect to the object.

10 Claims, 7 Drawing Sheets

U.S. PATENT DOCUMENTS

| | | |
|---|---|---|
| 6,393,921 B1 | 5/2002 | Grimes et al. |
| 6,413,220 B1 | 7/2002 | Rose |
| 6,424,407 B1 | 7/2002 | Kinrot et al. |
| 6,583,630 B2 * | 6/2003 | Mendes et al. ............ 324/652 |
| 6,688,162 B2 * | 2/2004 | Bachas et al. ............ 73/64.42 |
| 2002/0143268 A1 | 10/2002 | Meredith et al. |
| 2002/0177790 A1 * | 11/2002 | Meredith et al. ............ 600/587 |
| 2004/0025593 A1 * | 2/2004 | Hashimoto et al. ............ 73/643 |
| 2004/0123665 A1 * | 7/2004 | Blodgett et al. ............ 73/579 |
| 2004/0204647 A1 | 10/2004 | Grupp et al. |
| 2005/0026113 A1 * | 2/2005 | Chen et al. ............ 433/173 |
| 2008/0199828 A1 * | 8/2008 | Pan et al. ............ 433/167 |

FOREIGN PATENT DOCUMENTS

| | | |
|---|---|---|
| EP | 0853938 A1 | 7/1998 |
| JP | 06-506371 | 7/1994 |
| JP | 08-089517 | 4/1996 |
| JP | 10-505519 | 6/1998 |
| JP | 03-070752 | 11/2003 |
| WO | 01/19248 | 3/2001 |
| WO | 01/22880 | 4/2001 |
| WO | 03/011133 | 2/2003 |

* cited by examiner

METHOD AND ARRANGEMENT RELATING TO TESTING OBJECTS

CROSS-REFERENCE TO RELATED APPLICATIONS

The present application is a Continuation-In-Part of U.S. application Ser. No. 10/561,362, which, in turn, is a National Stage filing under 35 U.S.C. §371 of PCT/SE04/00998 filed Jun. 21, 2004, which claims Paris Convention priority to Swedish Application No. SE 03-01825-6 filed Jun. 19, 2003. The disclosures of all three applications are incorporated herein by reference.

TECHNICAL FIELD

The present invention relates to a method and apparatus for testing an object, such as an implant attached to a bone of a human or animal subject.

BACKGROUND

The use of implants involves the insertion of a metal fixture into a prepared hole in the bone. During the healing process, the surrounding bone develops an intimate contact with the implant surface and after a suitable time a prosthesis may be attached to the fixture. Such implants are frequently used in dentistry and in cosmetic surgery.

There is a need for a means of clinically observing the quality of the union between the bone and the implant surface. Implant failures can be caused by errors in placement, and premature or inappropriate loading. A non-destructive test, which could be used before loading the implant would help to reduce failures of this type, and would also enable periodic tests to be carried out on implants which are in use to ensure that they are still satisfactory. The test could also provide a quantitative comparison between different implant systems.

X-rays are sometimes used to test the condition of an implant, but they can only show the presence of gross bone loss around the implant. It is also very difficult to monitor the progress of integration over time with x-rays, since it is difficult to reproduce the viewing position and angle with sufficient accuracy. A different sort of test, albeit a crude one, is to tap the structure attached to the implant with a surgical instrument. This test can only distinguish between satisfactory implants and the most grossly defective systems.

When a resonance frequency is used in order to determine the stiffness of the bone-implant interface, the transducers used may have different properties between individual transducers and between different types of transducers.

The difference must be calibrated for, to achieve comparable results from different measurements.

The calibrations are normally made by measuring the resonance frequency on one calibration block, which is determined to give a nominal resonance frequency. The difference to this nominal value is then either subtracted or added to all later measured values with this transducer.

The approach has some disadvantages: it is assumed that all transducers had the same sensitivity, and that the difference between them is only an offset problem, thereby making it possible to only calibrate the relationship between them for one specific stability.

The early studies mainly used the same transducer to follow a specific implant, and the focus was on the change of resonance frequency, and not on the absolute value. It could be difficult however, to compare results between different patients or studies. Another disadvantage is that the frequency scale (measured in Hz) is a bit difficult to communicate, which may be a scale from approximately 3000 Hz to 9000 Hz.

To solve the above mentioned problem, a new index has been established, ISQ (Implant Stability Quotient). ISQ runs from 1 to 100, and is a close to linear mapping of the Hz-scale.

ISQ is defined by a set of calibration blocks with different stability. All transducers are calibrated on these blocks, and the calibration parameters are programmed into the transducer plug. That way, all transducers will give the same ISQ for the same stability, thus making it possible to compare results between different transducers. Also, there is no need to calibrate the transducers before each measurement occasion, since the transducer is carrying the parameters with it.

Mathematically, ISQ is defined by the following equation:

$$ISQ = FR * FR(u + v*L) + FR*(k + n*L) + p + m*L.$$

Where
FR is measured resonance frequency
u, v, k, n, p, m are calibration factors −1 to +1 (resolution 2/32768), and
L is abutment length (for an abutment transducer)

The six parameters u, v, k, n, m and p may all be programmed into each transducer plug.

To determine the relationship between ISQ and frequency (Hz) for the first time, some transducers from the early clinical studies were used. Five calibration blocks with different stability were manufactured, and the spread in resonance frequency between the blocks where equal to the spread seen in the clinical studies. The relationship between resonance frequency and ISQ was then determined to be linear on these blocks with those transducers, and the end points on the block with the lowest stability and the block with the highest stability were decided. The end points were decided in such a way so that 1 ISQ or 100 ISQ corresponds to a stability outside what had been seen in clinical practice.

After the ISQ-values on the five calibration blocks were decided, they were determined to serve as a standard, when all future types of transducers were manufactured.

The resonance frequency of the transducers was measured by feeding a piezoelectric crystal, attached to the transducer beam, with sinusoidal signal which was swept from approximately 3 to 10 kHz during a couple of seconds. Another crystal, attached to the other side of the beam, measures the voltage, and thus the amplitude, during the sweep. When the swept sinus reaches the resonance frequency of the beam, the output from the second crystal has its maximum.

The International Patent Application No. WO 92/18053, relates to a method of testing an implant attached to a bone of a human or animal subject. The method comprises the steps of bringing a member into contact with the implant; detecting at least one resonance frequency of the member when it is in contact with the implant; and interpreting the detected resonance frequency in terms of the degree of attachment of the implant with respect to the bone. However, the method implies using an analyzing unit being in contact with the implant through a wire.

U.S. Pat. No. 3,355,933 and WO 99/46603 relate to measuring arrangements for measuring surface vibrations of a large object. The arrangements presented in these documents are not suitable for small spaces, such as a mouth of a patient.

SUMMARY OF THE INVENTION

One object of the present invention is to provide contactless testing apparatus and method of an object, especially an object in a small space such as an implant.

Another object of the present invention to provide a non-destructive test, which is capable of giving a reliable indication of the quality and/or extent of the union between an implant and the bone to which it is attached in a contactless way.

Another object of the present invention is to provide a testing arrangement, which is disposable providing a purity aspect to the invention.

For these reasons, a method and arrangement for testing an implant attached to an object, such as a bone, are provided. The method comprises the steps of: bringing a member into contact with the implant, contactlessly detecting at least one resonance frequency of the member when it is in contact with the implant and interpreting the detected resonance frequency in terms of the degree of attachment of the implant with respect to the bone. The method further comprises the step of detachably attaching the member to the implant. Preferably the member comprises a cantilever beam.

According to one embodiment of the invention the member comprises a magnetic part. Thus, the resonance frequency is detected by means of a coil.

According to another embodiment, the member comprises a marking. Thus, the resonance frequency is detected by means of an illumination detector.

According to another embodiment of the invention, the member is made of a ferromagnetic material. Thus, the resonance frequency is detected by means of the member disturbing a magnetic field.

Preferably, the implant includes a threaded bore, and the cantilever beam is screwed to or into the implant.

The method further comprises the step of comparing the detected resonance frequency with one or more values for the resonance frequencies of the same or similar members in contact with other implants. In one step, the detected resonance frequency is compared with one or more values, taken at different times, for the resonance frequencies of the same or similar member in contact with the same implant.

The method further includes the steps of exciting the member with a force, detecting the response of the member to the force and deriving an output, which is the ratio of the voltage of the response signal to that of the excitation signal.

The invention also relates to an arrangement for testing an implant attached to a bone. The arrangement comprises: a member adapted to be releasable attached to the implant, and detecting means for detecting at least one resonance frequency of the member when it is attached to the implant. The member comprises a detectable part. The detecting means comprises a detector for contactless detection of the detectable part.

According to one embodiment, the detectable part comprises a magnetic member. Thus, the detector comprises a coil. The arrangement further comprises an amplifier, a processor, and a data store. The signals detected by the detector are amplified by the amplifier and applied as an input to be analyzed. The analyzed output, which represents a ratio of a response voltage to the excitation, is fed to the processor, which varies the frequency output of the oscillator of the analyzer, and stores the results in the data store.

According to another aspect of the invention, the detectable part comprises a marker. Thus, the detector comprises an illumination detector and an illuminator.

According to another aspect of the invention, the detectable part consists of a ferromagnetic material.

According to another aspect of the invention, the detector comprises a coil for detecting disturbances in an external magnetic field.

Preferably the member comprises a cantilever beam. Advantageously, the beam is arranged or adapted to resonate at a frequency within the range of about 1 to 20 kHz, preferably about 1 to 10 kHz, and more preferably of the order of about 8 kHz.

For sanitary reasons the member is disposable.

The invention also relates to a disposable implant testing part provided for testing an implant attached to a bone. The disposable implant testing part comprises a detectable part, which can be detected contactless by means of a detector.

The invention also relates to a testing equipment for testing an implant configured to be attached to a bone. The testing equipment comprising: a probe portion adapted to be positioned spaced from the implant in vicinity of the implant and comprising an electromagnetic detection part, a signal processing unit being configured to receive a signal from the electromagnetic detection part, an output arrangement configured to output a result from the signal processing unit. The result corresponds to a resonance frequency of the implant, which represents a ratio of a response voltage when a magnetic part coupled to the implant is excited. The signal processing unit is further configured to vary a frequency output of an oscillator, and stores the results in the data storing arrangement. The equipment may further comprise at least one coil configured to output magnetic pulses to a member attached to the implant and detect responses corresponding to the magnetic pulses from the member. The pulses are overlapping and narrow band and cover a frequency spectrum.

BRIEF DESCRIPTION OF THE DRAWINGS

The invention will now be further described, by way of example only, with reference to the accompanying drawings, in which.

DETAILED DESCRIPTION

Figure 1:
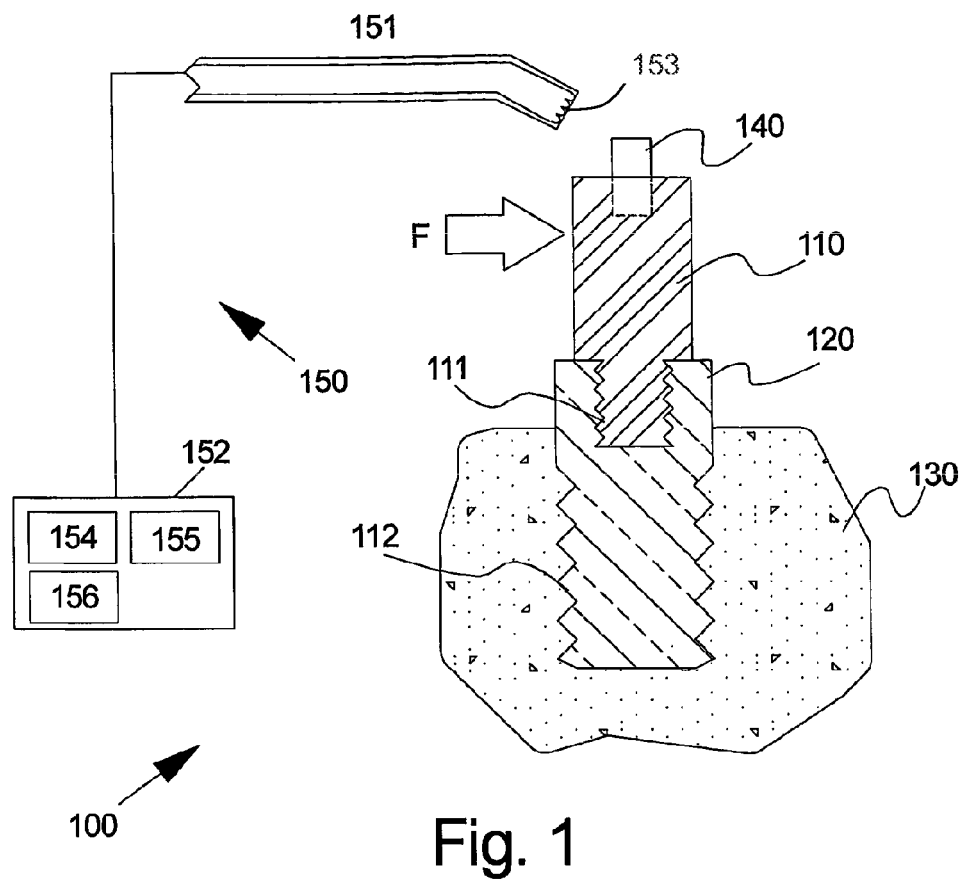
FIG. 1 is a schematic cross-sectional view of one embodiment of an implant testing member and apparatus according to the first aspect of the invention.

Referring to FIG. 1, the apparatus 100 comprises two parts, a member 110 in the form of a cantilever beam attached by means of a threaded section 111 to an implanted fixture 120. The implant fixture can be a dental implant attached by a threaded section 112 in a section of a bone 130, typically a human jawbone or any other type of an implant for humans or animals. The implant 120 may be any one of a number of known types, formed from a metal, such as titanium, from a ceramic material, or any other appropriate material. It may, for example, be of the type supplied by Nobel Biocare in the U.K. The member 110 is provided with a magnetic member 140. The magnetic member 140 can be provided at one end of the beam 110, e.g. the free end or integrated inside the beam.

The second part of the apparatus comprises the testing apparatus 150, including a probe 151 and a response analyzer unit 152. The probe 150 comprises a coil 153 for detecting oscillations of the magnetic member.

To generate oscillations in the beam, it must be excited. This can be done manually or by means of an electrical exciter, through application of a force F on the beam.

Signals detected by the probe 151 are amplified by an amplifier 154 and applied as an input to the analyzer. The output from the analyzer, which represents the ratio of the response voltage to the excitation, is fed to a processor such as a microprocessor 155, which is used to vary the frequency output of the oscillator of the analyzer, and store the results in a data store 156. The results can be printed out, and/or displayed on a display or the like.

Figure 2:
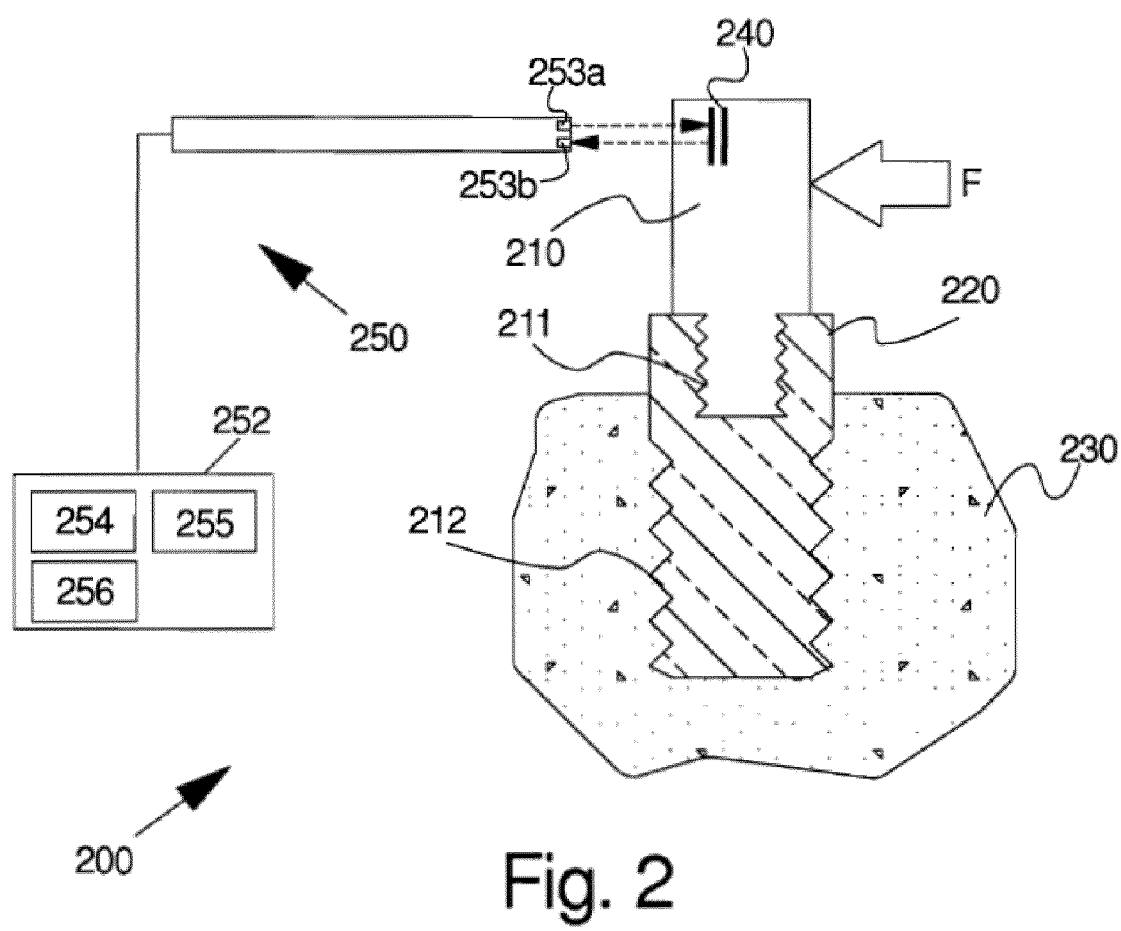
FIG. 2 is a schematic cross-sectional view of one embodiment of an implant testing member and apparatus according to the second aspect of the invention.

Referring now to FIG. 2, illustrating a second embodiment of the invention, the first part of the arrangement 200 according to the invention comprises, a member 210 in the form of a cantilever beam as in the earlier embodiment attached by means of a threaded section 211 to the implanted fixture 220. Also, in this case, the implant fixture can be a dental implant attached by a threaded section 212 in a section of a bone 230. The member 210 in this case is provided with markings 240, such as lines, arranged at one end of the beam 210.

The second part of the arrangement comprises the testing apparatus 250, including a probe 251 and a response analyzer unit 252. The probe 250 comprises a light source 253a, preferably but not exclusively a laser, and a light detector 253b for detecting reflections from the beam and thus oscillations of the beam. The light source is preferably Laser diode. The beam is provided with one or several markers, such as darker (or lighter) sections, which effect the reflection of the light.

The beam is excited manually or e.g. by means of an electrical exciter, by applying the force F on the beam.

The light source on the tip of the probe illuminates the beam and the light detector 253b detects the reflected light. The detected light signal is converted to an electrical signal by the detector, and signals detected by the probe 251 are amplified by an amplifier 254 and applied as an input to the analyzer. The output from the analyzer, which represents the ratio of the response voltage to the excitation, is fed to a processor such as a microprocessor 255, which is used to vary the frequency output of the oscillator of the analyzer, and store the results in a data store 256. The results can be printed out, and/or displayed on a display or the like.

In use the beam 110 is secured, i.e. screwed, to the implanted implant 120 with a predetermined torque, for example using a torque controller and counter tool. The variations in resonance frequency with torque have been found to be relatively small over a practical range of torques, for example of the order of 5 to 10 Ncm, so that such torque variations should not present a problem.

Preferably, but not necessarily, the beam according to the invention is disposable, which means that it can be screwed off and disposed, providing a hygienic testing arrangement.

Figure 3:
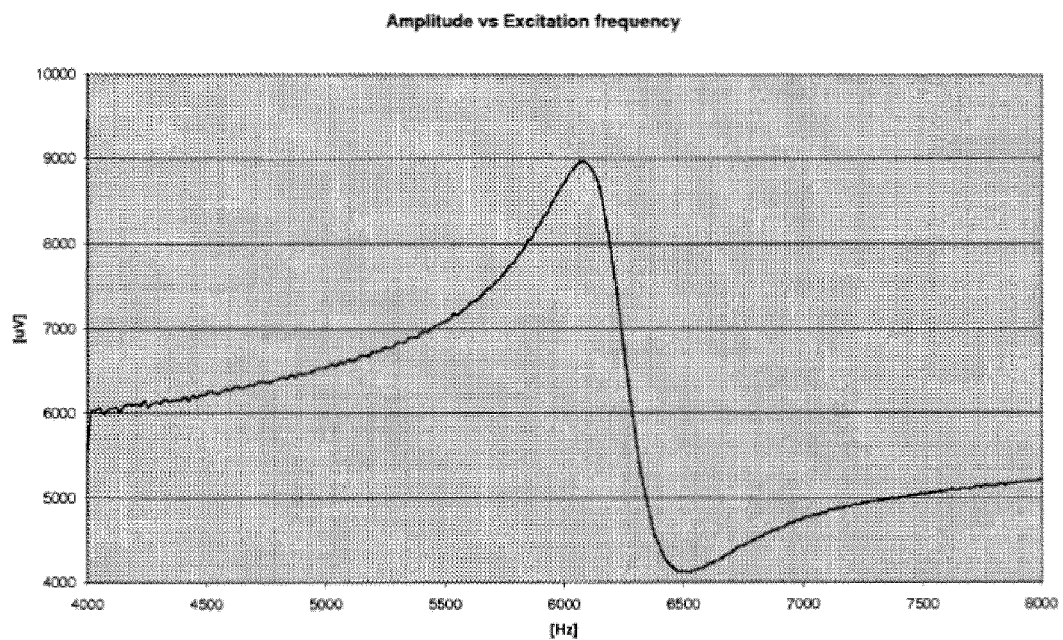
FIG. 3 is a graphical representation of the hypothetical change in the received amplitude with respect to the frequency of a testing beam according to the invention attached to a typical implant.
Figure 4:
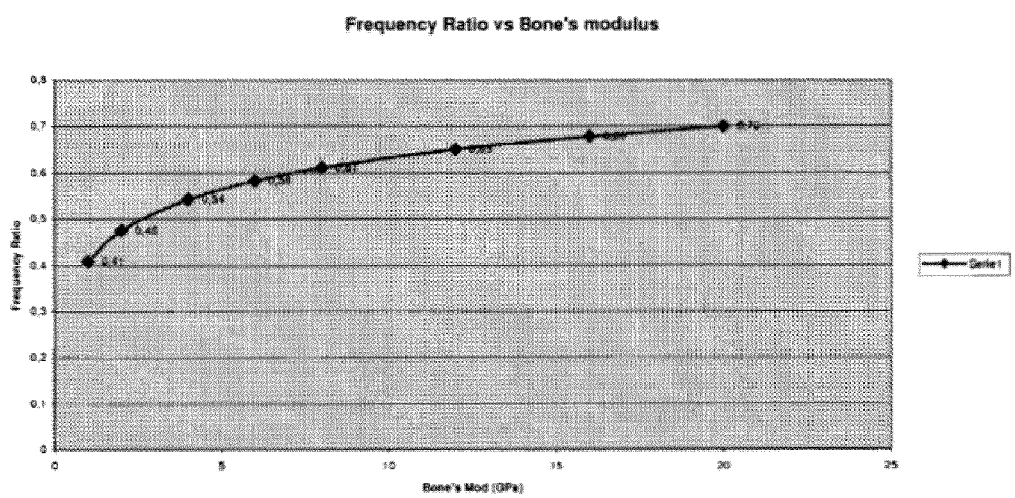
FIG. 4 is a graphical representation of the hypothetical change in the relative frequency with respect to the bone modulus of the testing beam according to the invention.

FIG. 3 shows the data from a coarse sweep, which is used to obtain the resonance frequency roughly in the apparatus of FIG. 1. A finer sweep around this region is then used to identify this frequency, typically the first or fundamental frequency, more accurately. This frequency is noted, and compared, for example, with the data for other implants at similar stages of bonding.

It is expected that for a particular implant, the resonance frequency will vary with the degree of attachment to the bone.

Thus by comparing the detected resonance frequency with previously compiled data for similar implants, an indication of the degree of attachment of the implant can be obtained.

The technique, which is based on detection and comparison of resonance frequency shifts, rather than amplitude changes, is effective to determine the quality of the implant/tissue interface as a function of its stiffness, and also in relation to any bone loss as a function of the level or height of the marginal bone surrounding the implant.

The beam is preferably of a metallic material, for example titanium or aluminium, is dimensioned so as to provide a resonant frequency range of the system (placed implant and beam) of the order of 1 to 20 kHz, more specifically 1 to 10 kHz, and preferably in the region of about 8 KHz. For example, in the embodiment of FIG. 1, the upright beam can be approximately 1 cm high.

Figure 5:
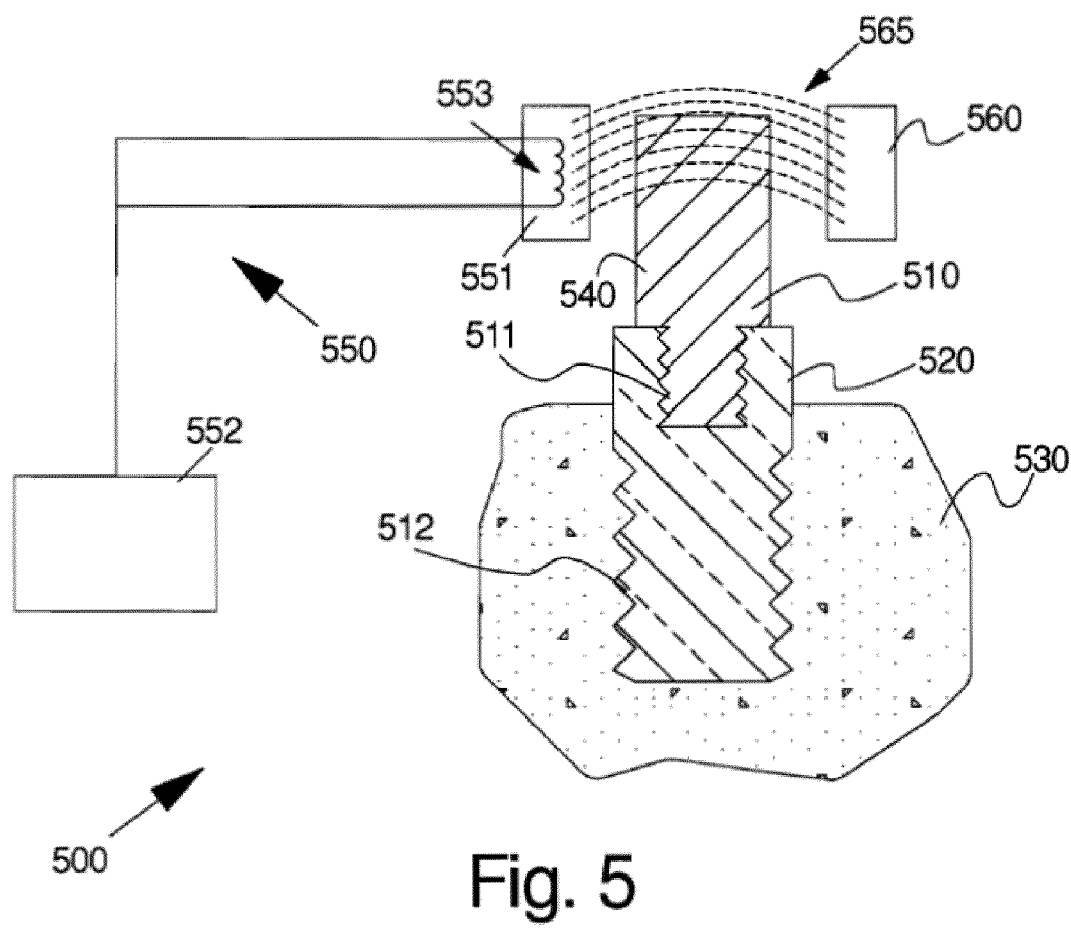
FIG. 5 is a schematic cross-sectional view of one embodiment of an implant testing member and apparatus according to the third aspect of the invention.

In yet another embodiment, as illustrated in FIG. 5, the first part of the arrangement 500 according to this aspect of the invention comprises a member 510 in the form of a cantilever beam made of a ferromagnetic material attached by means of the threaded section 511 to the implanted fixture 520. Also, in this case, the implant fixture can be a dental implant attached by a threaded section 512 in a section of a bone 530. Thus, the member 510 in this case is itself the detectable part 540.

The beam 510 is brought into excitation by means of an external magnetic field 565 generated by the field generators 560.

The testing apparatus 550 includes the probe 551 and the response analyzer unit 552. The probe can be part of the magnetic field generator. The probe 550 comprises a coil 553 for detecting interferences in the magnetic field 565. The analyzing can be conducted as described in conjunction with the first embodiment.

The field generator can be a permanent magnet for generating a DC field or a coil for generating an AC filed. The probe may also be externally arranged.

According to one aspect of the invention, the former transducers may be replaced with beams or pegs 110 (FIG. 1), which are screwed onto the implant or an abutment. The resonance frequency of these pegs is measured by the electronics, the same principle as described earlier in conjunction with embodiment of FIG. 1.

While a transducer according to prior art is fed by a swept sinusoidal signal, the magnet attached to a smart peg is excited with magnetic pulses. After each pulse, the alternating magnetic field that is the result of the self-vibrating peg, is picked up by the electric coil in the measurement probe. The magnetic pulses may be generated by another coil in the same probe (or an additional probe).

The metal pegs have a simplified mechanical design compared to the transducers, and do not require individual calibration. It is not possible to store any calibration parameters in them since they are not electrically connected to the instrument. Instead, the individual differences between pegs are reduced to a minimum by a carefully controlled manufacturing process.

The pegs also have a simpler mechanical behavior when they are vibrating at their resonance frequency. They are more sensitive and have a predictable behavior down to very low implant stability.

When comparing the prior art transducer ISQ to the peg ISQ according to the present invention, the latter uses the ISQ scale better, in that it is possible to get an ISQ down to ISQ 1, while the transducer is not working at such low stabilities.

With the peg according to the present invention, the differences in ISQ between different implant systems are minimized.

The pegs are symmetrical and vibrate at two frequencies simultaneously. These two frequencies correspond to the lowest and the highest stability direction for a specific implant (the directions are normally perpendicular to each other). To be sure to measure both these stabilities, it is important to make two measurements on each implant, holding the probe from two different directions.

This means that two values can be achieved on each implant (sometimes these values can be the same, for an implant with symmetrical stability).

The lowest and highest stability directions correspond normally to the bucco-lingual and the mesio-distal direction, respectively.

Figure 6A:
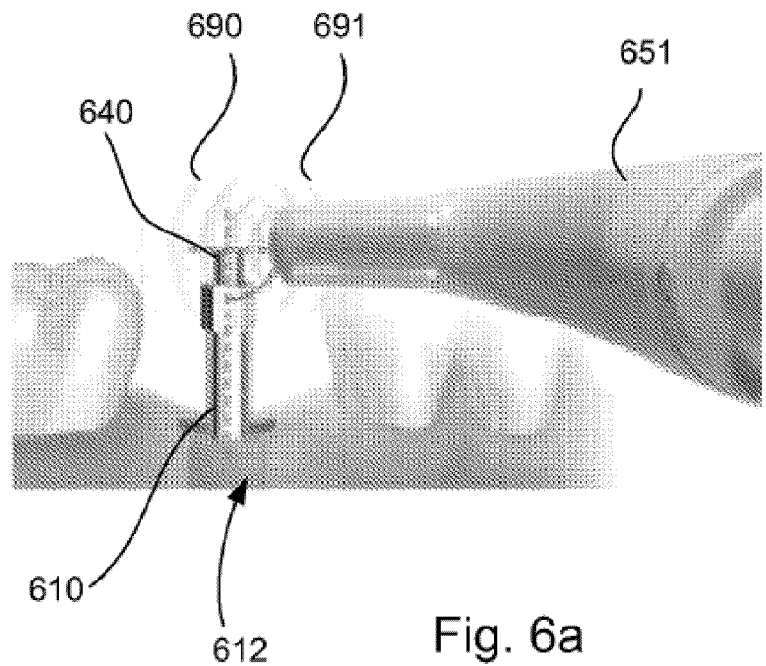
FIGS. 6a-6c illustrate contactless measurements according to one embodiment of the invention.
Figure 6B:
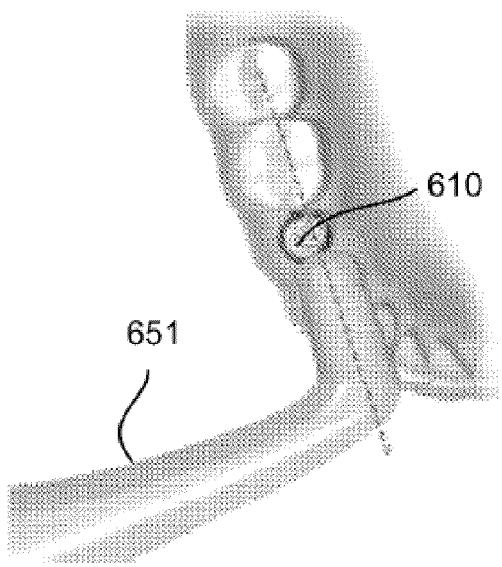
Figure 6C:
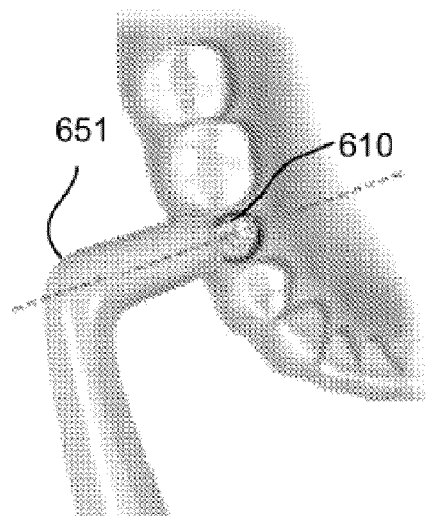

FIGS. 6a-6c illustrates measurement views. In FIG. 6a a peg 610 is attached to a dental implant 612. The peg 610 comprises a magnetic portion 640. The probe 651 is brought to the vicinity of the peg 610 and applies an electromagnetic force 690. The response from of resonance frequency 691 of the peg is detected by the same probe 651. The probe 651 may have one or several coils.

Preferably, two measurements are performed with the device, one with the probe 651 in the mesio-distal direction towards the peg 610, FIG. 6b, and one with the probe 651 in the bucco-lingual direction, FIG. 6c. If there are difficulties in getting the two different ISQ-values, the rotational position can be changed slightly from these two directions.

Figure 7A:
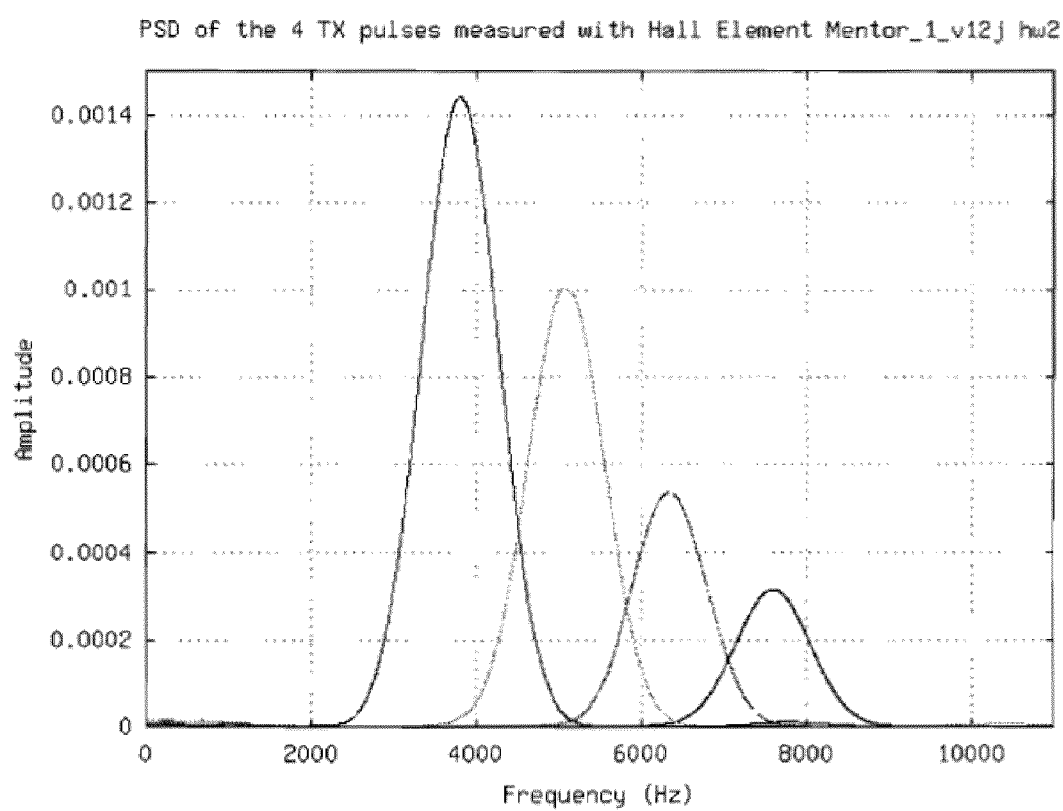
FIGS. 7a and 7b are graphical representations output pulse from a device according to one embodiment of the invention.
Figure 7B:
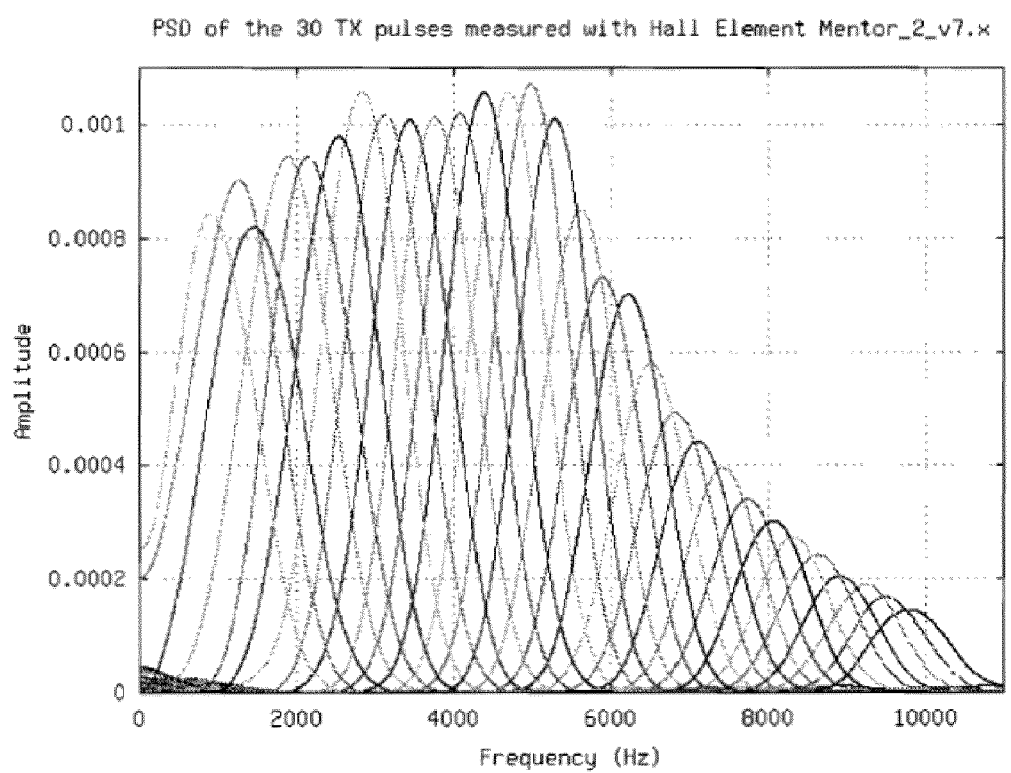

A measurement may consist of a number of pulses, e.g. 4 or 30 pulses as illustrated in graph of FIGS. 7a and 7b, respectively. In the case of 30 pulses, these pulses cover the frequency spectrum from 1 to 10 kHz. Since the pulses are more narrow-band, the 30 pulses contain more energy. This makes the responding signal stronger, and the signal to noise ratio is improved, making the measuring device of the invention less sensitive to surrounding electromagnetic noise. It is recognized by a skilled person that the number of pulses are not limited to 4 or 30.

It will be understood that various modifications may be made without departing from the scope of the present invention as defined in the appended claims.

The transducers or gauges, and optionally also the beam may be coated, for example with an air-dry acrylic material, to protect the transducers during sterilization of the apparatus. The member may take a form other than a cantilever beam. The beam, instead of being basically straight, could be generally U-shaped, and connected to the implant or abutment by its base. Moreover, alternative detectors, such UV, sound, and the like can also be used.

The invention is not limited to implants and can be applied in preferably all small spaces wherein hold of an object such as screws, rivets, bolt or pin, is to be tested.

What is claimed is:

1. A method of testing an implant, attached to a bone, the method comprising the steps of:
   bringing a detachable member attached to said implant into vibration by applying a magnetic pulse to a magnet attached to said member with a probe spaced apart from said member;
   contactlessly detecting two resonance frequencies of said member using the probe based on an alternating magnetic field resulting from the vibrating member, wherein the two resonance frequencies correspond to lowest and highest stability directions for the implant, and wherein the lowest stability direction is a bucco-lingual direction and the highest stability direction is a mesio-distal direction; and
   interpreting the detected resonance frequencies in terms of the degree of attachment of the implant to the bone.

2. The method according to claim 1, including the step of detachably attaching said member to said implant.

3. The method according to claim 1, wherein said member comprises a cantilever beam.

4. The method according to claim 3, wherein said implant includes a threaded bore, and said cantilever beam is screwed to or into the implant.

5. The method according to claim 1, wherein said member comprises a magnetic part and said resonance frequencies are detected by means of a coil.

6. The method according to claim 1, wherein said member is made of a ferromagnetic material.

7. The method according to claim 6, wherein said resonance frequencies are detected by means of said member disturbing a magnetic field.

8. The method according to claim 1, comprising the step of comparing the detected resonance frequencies with one or more values for the resonance frequencies of the same or similar members in contact with the same or other implants.

9. The method according to claim 1, comprising the steps of exciting the member with a magnetic pulse and detecting the response of the member to the magnetic pulse.

10. A method according to claim 9, comprising deriving an output which is the ratio of the voltage of the response signal to that of an excitation signal.

\* \* \* \* \*